United States Patent
Han et al.

(10) Patent No.: US 6,938,458 B2
(45) Date of Patent: Sep. 6, 2005

(54) ACOUSTIC DOPPLER DOWNHOLE FLUID FLOW MEASUREMENT

(75) Inventors: Wei Han, Missouri City, TX (US); Jean M. Beique, Houston, TX (US); James R. Birchak, Spring, TX (US); Alan T. Hemphill, Sugar Land, TX (US); Tim Wiemers, Houston, TX (US); Paul F. Rodney, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 10/882,421

(22) Filed: Jul. 1, 2004

(65) Prior Publication Data

US 2005/0034530 A1 Feb. 17, 2005

Related U.S. Application Data

(62) Division of application No. 10/437,597, filed on May 14, 2003, now Pat. No. 6,829,947.
(60) Provisional application No. 60/380,648, filed on May 15, 2002.

(51) Int. Cl.$^7$ .............................................. G01N 33/24
(52) U.S. Cl. ....................................................... 73/19.09
(58) Field of Search ............................... 73/19.09, 19.1, 73/19.03, 152.04; 181/102; 175/40

(56) References Cited

U.S. PATENT DOCUMENTS

| | | | |
|---|---|---|---|
| 2,745,282 A | * | 5/1956 | Rochon |
| 3,901,078 A | | 8/1975 | McShane |
| 4,527,425 A | | 7/1985 | Stockton |
| 4,733,233 A | * | 3/1988 | Grosso et al. ................ 367/82 |
| 4,754,641 A | | 7/1988 | Orban et al. |
| 4,979,112 A | | 12/1990 | Ketcham |
| 5,353,873 A | | 10/1994 | Cooke, Jr. |
| 5,700,952 A | | 12/1997 | Andersen |
| 5,831,156 A | | 11/1998 | Mullins |
| 5,924,499 A | * | 7/1999 | Birchak et al. ................ 175/40 |
| 5,969,638 A | * | 10/1999 | Chin ....................... 340/855.3 |
| 6,067,861 A | | 5/2000 | Shekarriz et al. |
| 6,092,416 A | | 7/2000 | Halford et al. |
| 6,257,354 B1 | | 7/2001 | Schrader et al. |
| 6,296,385 B1 | | 10/2001 | Balasubramaniam et al. |
| 6,354,146 B1 | | 3/2002 | Birchak et al. |
| 6,581,454 B1 | | 6/2003 | Smith |
| 6,672,163 B2 | | 1/2004 | Han et al. |
| 6,817,229 B2 | | 11/2004 | Han et al. |

FOREIGN PATENT DOCUMENTS

US    PCT/US03/15232    9/2003

OTHER PUBLICATIONS

Arrian et al., ABBAS, "MWD Ultrasonic Caliper Advanced Detection Techniques," SPWLA 39th Annual Logging Symposium, May 26–29, 1998, pp. 1–14.

(Continued)

*Primary Examiner*—Robert Raevis
(74) *Attorney, Agent, or Firm*—Conley Rose, P.C.

(57) ABSTRACT

An apparatus and system are disclosed for in situ measurement of downhole fluid flow using Doppler techniques. First, a baseline speed of sound is established as close to the desired measurement point as possible. This speed of sound measurement is then used in Doppler calculations for determining flow velocities based from induced Doppler shift resulting from fluid flow. A heterodyne receiver arrangement is preferably used for processing so that the flow direction can be determined and the detection sensitivity for low flow velocities can be enhanced. From in situ measurements, well kicks may be spotted and dealt with in real-time. In addition, current theoretical models of rheological properties may be verified and expounded upon using in situ downhole measurement techniques. Furthermore, the velocity measurements described herein can be used to recognize downhole lost circulation and/or gas/water/oil influxes as early as possible, even when the mud recirculation pumps are turned off.

4 Claims, 5 Drawing Sheets

OTHER PUBLICATIONS

Han, Wei and Pendse, Hemant P., "Unified Coupled Phase Continuum Model for Acoustic Attenuation in Concentrated Dispersions," Ultrasonic and Dielectric Characterization Techniques for Suspended Particulates, pp. 129–152. Published by The American Ceramic Society of Westerville, Ohio, USA.

Jellison et al., Michael J., "Telemetry Drill Pipe: Enabling Technology for the Downhole Internet," Society of Petroleum Engineers, IADC/SPE Drilling Conference, Feb. 19–21, 2003, 10 pgs., Amsterdam.

Loeppke et al., Glen E., "Development And Evaluation Of A Meter For Measuring Return Line Fluid Flow Rates During Drilling," SAND 91–2607, Jun., 1992, pp. ii–28.

Molz et al., Eric, "Ultrasonic Velocity and Attenuation Measurments in High Density Drilling Muds," SPWLA 39th Annual Logging Symposium, May 26–29, 1998, pp. 1–8.

Verrall et al, R.E., "Sound Velocity Studies of Pipeline Oils as a Function of Viscosity, Density and Water Content," The Journal of Canadian Petroleum Technology, University of Saskatchewan, pp. 51–57, Feb., 1994, vol. 33.

* cited by examiner

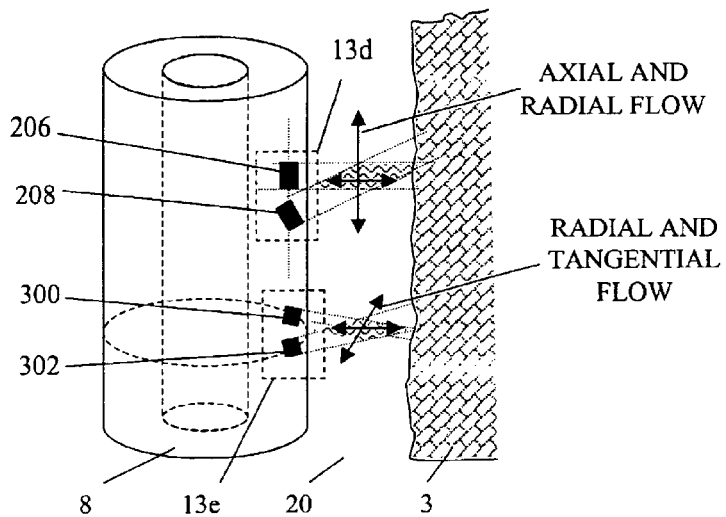
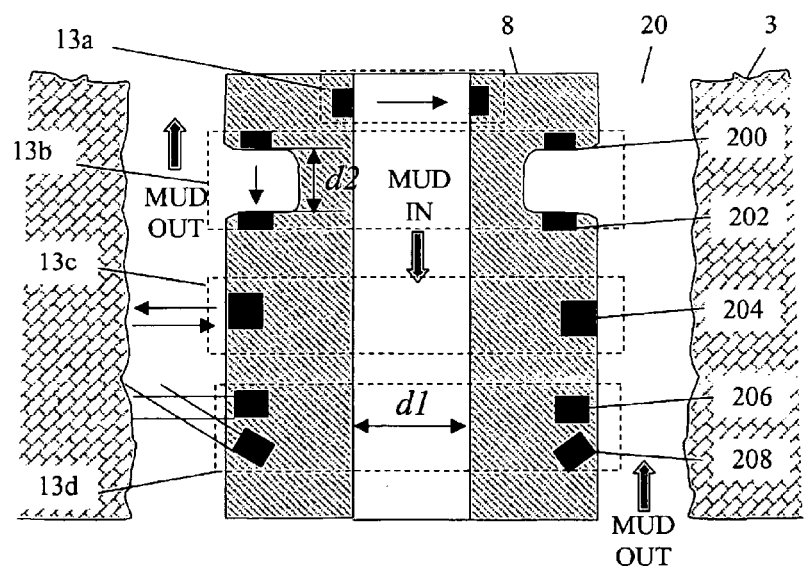

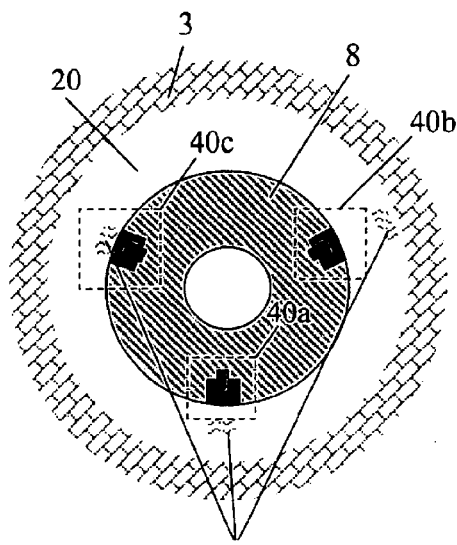
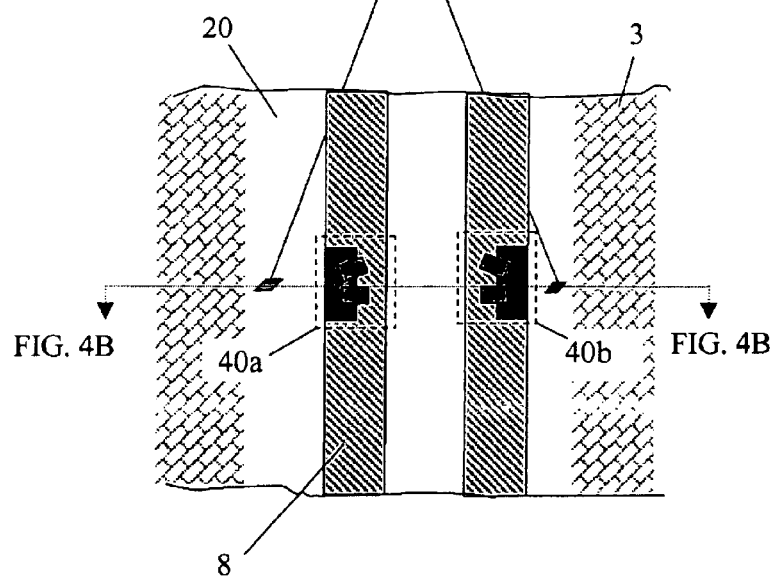

ACOUSTIC DOPPLER DOWNHOLE FLUID FLOW MEASUREMENT

CROSS-REFERENCE TO RELATED APPLICATIONS

This application is a divisional from application Ser. No. 10/437,597, entitled "Acoustic Doppler Downhole Flow Measurement", filed May 14, 2003, now U.S. Pat. 6,829,947 and incorporated herein by reference. The foregoing parent application claims priority to Provisional Application Ser. No. 60/380,648, entitled "Acoustic Doppler Downhole Flow Measurement", filed May 15, 2002, and incorporated herein by reference.

This application is related to commonly owned U.S. Pat. No. 6,378,357, entitled "Method of Fluid Rheology Characterization and Apparatus Therefor", issued Apr. 30, 2002, and incorporated herein by reference.

STATEMENT REGARDING FEDERALLY SPONSORED RESEARCH OR DEVELOPMENT

Not applicable.

BACKGROUND OF THE INVENTION

Conventional drilling techniques often employ drilling fluid (termed "mud") that is circulated downhole for various reasons such as carrying earth cuttings out of the wellbore, cooling the drill bit, and also to control pressure in the well. The mud is pumped downhole through the drillstring, where it exits at the bottom of the drill bit and is forced to the surface in the annular space between the drillstring and the wellbore (hereinafter "annulus"). The hydrostatic pressure exerted by the mud column is the primary method of controlling the pressure in the formation. Loss of pressure and circulation problems may occur due to the mud being lost to the formation rather than circulating back to the surface. Although drilling can continue under these adverse conditions, it is important that lost circulation be detected as early as possible for safety and well control reasons.

First, is that drilling fluid is expensive (e.g. $50–$300 per barrel), and pumping thousands of barrels into the formation drastically increases drilling costs and may cause formation damage. Second, if the circulation downhole is lost, the cuttings are not removed from the wellbore, and surface interpretation of changes in the rock formation cannot be detected. Also if downhole circulation is lost and cuttings are not removed from the hole, the cuttings may "settle" in the wellbore, thereby "sticking the drillstring" in the hole. Third, when the formation pressure exceeds the hydrostatic pressure exerted by the mud column, a "well kick" may occur where formation fluid unexpectedly enters the well. Uncontrolled fluid entry from the formation can lead to a dangerous condition known as a "well blowout." Thus, a method and apparatus for detecting and monitoring fluid flow downhole at any point along the drillstring would be very desirable.

Presently, technologies such as surface monitoring of the level of mud in the mud pit, or measuring the mud inlets and return lines are employed. Loeppke et al., describes a rolling counterbalanced float flowmeter to be used in the return lines in "Development and Evaluation of a Meter for Measuring Return Line Fluid Flow Rates During Drilling," Report SAND91-2607, Sandia National Laboratories, Albuquerque, N.Mex. (June, 1992). U.S. Pat. No. 6,257,354 issued on Jul. 10, 2001 to Schrader et al., details a flow velocity sensor for mud return line measurement. However, these surface measuring technologies fail to provide timely response to a well kick deep in the well because of the amount of travel time it takes for the pressure transients in the mud to reach the surface.

U.S. Pat. No. 4,527,425 issued on Jul. 9, 1985 to Stockton (hereinafter '425) discloses a down-hole mud flow rate detector consisting of an acoustic transmit-receive pair positioned on the outer wall of the drillstring to measure return mud flow rate in the annulus and another transmit receive pair on the inner wall of a drill string to measure incoming mud flow rate. Differences in the acoustic transit time between up-stream and down-stream directions along the incoming mud flow and return mud flow are measured and used to determine the averaged flow velocities inside the drill pipe and in the annulus. However, this "transmit-time" method may be subject to several possible problems. First, the pulse wave from the transmitter is non-directional to the receiver and thus may be subject to beam diffraction and acoustic attenuation in the fluids along the path lengths. Second, the received waveform likely has a formation echo train which may consist of fast compression wave, slow compression wave, shear wave, or Stoneley wave that may interfere or overlap with the fluid echo and can make accurate determination of timing of the fluid echo very difficult. Third, invariably there are variations in the speeds of sound in the formations and/or the mud on both the incoming and return paths due to different pressures, temperatures, and unexpected fluid composition due to a well kick. This local variation in the speed of sound may exacerbate the aforementioned problems, thereby making accurate determination of the transmit time difference due to the annular flow even more difficult. Lastly, the transit time method taught in '425 only provides averaged velocity and not the full point-velocity profile across the annular gap.

In summary, conventional techniques do not provide in-situ measurements of the velocity profile of drilling mud within the wellbore or the direction of flow (i.e., target moving towards or receding from the transducers in the axial, radial, and tangential directions in the annulus).

SUMMARY OF THE INVENTION

The above-described problems are in large part addressed by an apparatus and system for in situ measurement of downhole fluid flow using Doppler techniques. A baseline speed of sound is first established close to the desired measurement point. Because the speed of sound can vary depending on pressure, temperature, and fluid composition, measuring the speed of sound close to the desired point may advantageously provide greatly enhanced accuracy. This speed of sound measurement is then used in Doppler calculations for determining flow velocities based on the Doppler shift induced by the fluid flow. A heterodyne receiver arrangement is preferably used for processing so that the flow direction can be determined and the detection sensitivity for "slow flow" velocities can be enhanced. This allows for more accurate estimation of flow velocities, which may be in the axial, radial, and/or tangential directions in the annulus. Accordingly, well kicks may be spotted and dealt with due to real time measurements. Porous formations may be identified by flow of the mud into the formation, and formation fractures (and orientations) may similarly be identified by fluid flow patterns. In addition, current theoretical models of rheological properties may be verified and expounded upon using in situ downhole measurement techniques. Furthermore, the problem of sticking the drillbit in the well is also addressed in that the velocity measurements can be used to assure adequate removal of cuttings from the wellbore, and corrective action can be taken if necessary to prevent the hole from being lost.

In an alternative embodiment, fractures in the formation may be detected. By monitoring the mud flow into a formation from the annulus at a fracture point, fracture orientation may be determined, including a three dimensional stress state characterization of the reservoir.

In yet another embodiment, baseline speeds of sound may be of made of the mud on the interior of the drillstring and the mud in the annulus can be measured. If there is a large difference in the two measurements, then this may indicate an influx in gas or fluid from the formation, which may further indicate a reservoir has been encountered.

In yet another embodiment, the disclosed sensors may be integrated along with repeater circuitry into a single package that is implemented at various points along the drillstring.

BRIEF DESCRIPTION OF THE DRAWINGS

A better understanding of the present invention can be obtained when the following detailed description of the embodiments are considered in conjunction with the following drawings, wherein like parts have been given like numbers:

FIG. 2 shows a preferred embodiment of an acoustic sensor arrangement;

FIG. 3 shows another embodiment of using acoustic sensors to measure flow velocities;

FIG. 4A shows a front view of sensors mounted around the circumference of the drillstring;

FIG. 4B shows a cross-section view of sensors mounted around the circumference of the drillstring;

Figure 1:
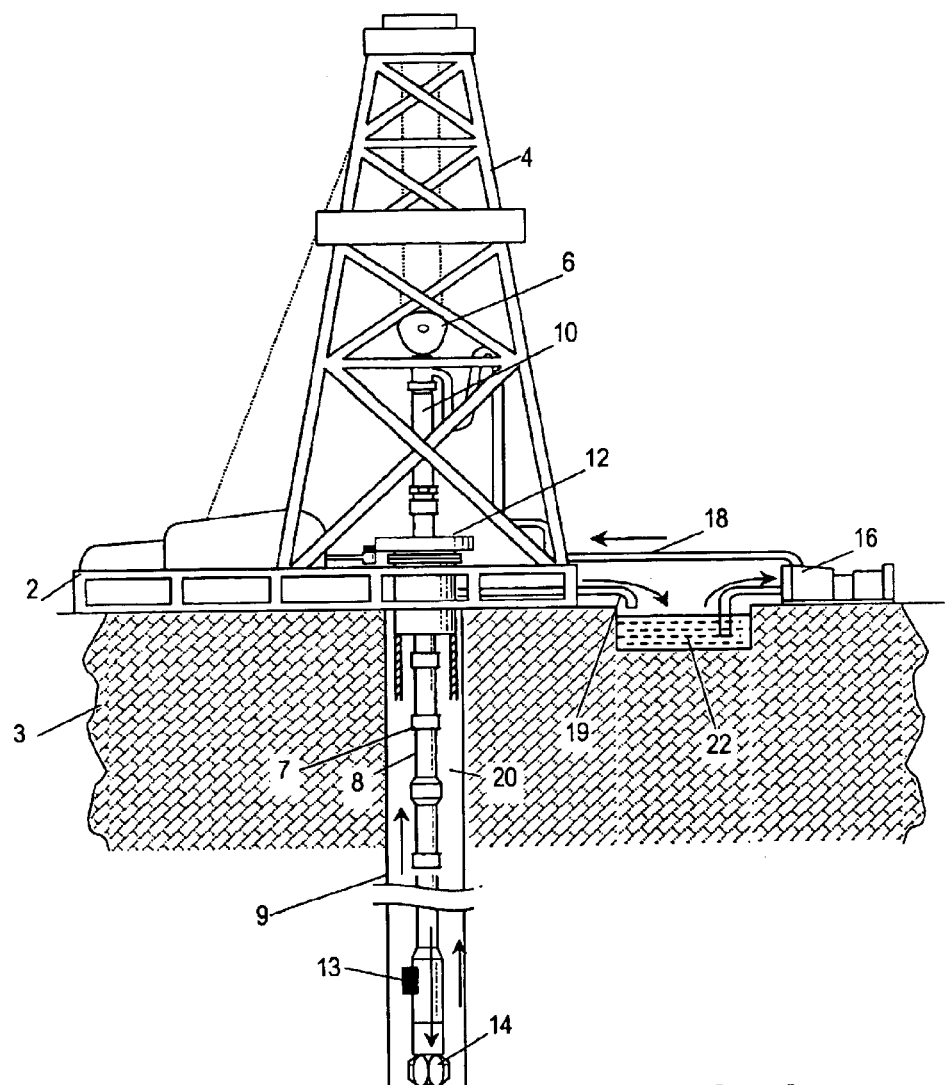
FIG. 1 shows a drilling rig including acoustic sensors.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

Referring now to the figures, FIG. 1A shows a well during drilling operations. A drilling platform 2 rests on a formation 3 and is further equipped with a derrick 4 that supports a hoist 6. Drilling of oil and gas wells is carried out by a string of drill pipes connected together by "tool" joints 7 so as to form a drillstring 8. The drillstring 8 is surrounded by a borehole wall 9. The hoist 6 suspends a kelly 10 that is used to lower the drill string 8 through rotary table 12. At least one sensor 13 is used in determining flow rates and velocity profiles and can be mounted anywhere along the drillstring 8. Connected to the lower end of the drill string 8 is a drill bit 14. The bit 14 is rotated and drilling accomplished by rotating the drill string 8, by use of a dowuhole motor near the drill bit, or by both methods. Drilling mud is pumped by mud recirculation equipment 16 through supply pipe 18, through drilling kelly 10, and down through the drillstring 8 at high pressures and volumes to emerge through nozzles or jets in the drill bit 14. The mud then travels back up the hole via an annulus 20 formed between the exterior of the drillstring 8 and the borehole wall 9 and enters a mud pit 24 on the surface through return pipe 19. On the surface, the drilling mud is cleaned and then recirculated by recirculation equipment 16. The drilling mud is used, among other things, to cool the drill bit 14, to carry cuttings from the base of the bore to the surface, and to balance the hydrostatic pressure in the formation 3 while drilling. Also the sensor 13 may be moved while in the borehole to measure mud properties at any point in the annulus 20.

FIG. 2 shows a cross sectional view of a preferred embodiment for the drillstring 8 including sensors 13a, 13b, 13c, and 13d which further include transducers. It should be noted that a transducer, as disclosed herein, may both produce and receive acoustic signals. Incoming mud is shown on the interior of the drillstring 8, and outgoing mud is shown in the annulus where it is measured by sensor arrangements 13a, 13b, 13c, and 13d. Note that although the mud is shown advancing in the annulus, it may actually be receding in the annulus, for example due to a loss of fluid to the formation. Sensor 13a is used to measure a baseline speed of sound of the mud inside the drill string, which is shown having an inner diameter of d1. Sensor 13b is used in measuring a baseline speed of sound measurement of the mud in the annulus. Sensor 13b preferably includes at least one acoustic transducer 200 located in a first circular plane and at least one acoustic transducer 202 located in a second circular plane, where the two circular planes are concentric with respect to the drillstring 8. The two circular planes are separated by a known distance d2. Preferably transducer 200 produces acoustic waves in the mud and transducer 202 receives these acoustic waves. Processing logic (not shown) determines the speed of sound based on the distance d2 (d1 for sensor 13a) and the time it takes to travel between the two transducers. The configuration of transmitting and receiving transducers may be reversed allowing the results under each scenario to be averaged thereby yielding a more accurate speed of sound measurement. Subsequently, this speed of sound measurement is used in calculating the direction and speed of fluid flow in the axial, radial, and tangential directions in the annulus.

As an alternative to the embodiment of FIG. 2, sensors 13a and 13b may be of the type disclosed in commonly owned U.S. patent application Ser. No. 09/851,511, filed on May 8, 2001, by Han et al., which is hereby incorporated by reference.

Referring still to FIG. 2, sensor 13c is preferably a pulse-echo arrangement including at least one transmit/receive transducer 204. Transducer 204 produces acoustic signals which travel radially through the annulus to the borehole wall and are reflected back to transducer 204. Processing logic (not shown) determines the annular gap using the speed of sound measurement from sensor 13b. Sensor 13d includes a transmitting transducer 206 and a receiving transducer 208. Transducer 206 is preferably oriented in an axial plane on the circumference of the drillstring 8 and emits acoustic signals radially into the annulus 20. Transducer 208 is oriented in the same axial plane on the circumference of the drillstring 8 and is further angled so as to receive acoustic signals that are Doppler shifted in frequency by the mud in the annulus. Processing logic (not shown) determines the axial velocity and direction of the mud in the annulus using the Doppler shifted signal from transducer 206 and the speed of sound measurement from sensor 13b. Thus, the transmit/receive pair 206 and 208 are able to measure the flow of mud in the axial direction in the annulus as well as determine its direction of travel (i.e., in or out of the annulus).

The transducers 200 through 208 are preferably piezo-electric or magnetic transducers that have a broad frequency response and support a wide frequency range, thus supporting signal propagation through different depths of investigation in the annulus. Note that sensor 13b should be located in close proximity to sensors 13c and 13d because the in situ speed of sound in the mud at different locations varies due to temperature, pressure, and fluid composition. Therefore, other methods which fail to take into account local speed of sound variations (e.g., look up tables based on laboratory data) will not yield as accurate of information as using an in situ speed of sound measurement.

Turning to FIG. 3, another embodiment of the sensor configuration is shown. Sensor 13d, as discussed previously, is shown measuring axial flow and direction in the annulus. Sensor 13e includes a transmitting transducer 300 and a receiving transducer 302. Transducer 300 is preferably oriented on a circular plane on the circumference of the drillstring 8 and is further angled such that it emits acoustic signals in an non-perpendicular direction into the annulus 20. Transducer 302 is oriented on the same circular plane on the circumference of the drillstring 8 and is angled so as to receive the acoustic signals transmitted by transducer 300, which have been Doppler shifted in frequency by the mud in the annulus. Processing logic (not shown) determines the radial velocity and direction of the mud in the annulus using the Doppler shifted signal and the baseline speed of sound measurement from sensor 13b.

FIGS. 4A and 4B show front view and cross sectional views respectively of the drillstring 8 including three sensors 40a, 40b, and 40c which operate at different frequencies allowing investigation at various radial depths. Sensors 40a, 40b, and 40c may be configured to measure axial flow and direction, radial flow and direction, or tangential flow and direction. For example, by configuring sensors 40a, 40b, and 40c like sensor 13e, radial flow and direction may be measured. Also, it is believed that higher transducer frequencies have better sensitivity and spatial resolution in shallow depths than the lower transducer frequencies. Accordingly, sensor 40a may be set around 250 kHz and used for velocity measurement at a radius about 3 inches from the drillstring 8. Sensor 40b may then be set around 1 MHz and used for velocity measurements around 0.75 inches from the drillstring. The third sensor 40c may then be set at around 4 MHz and used for velocity measurements around 0.3 inches from the drillstring 8.

Figure 5B:
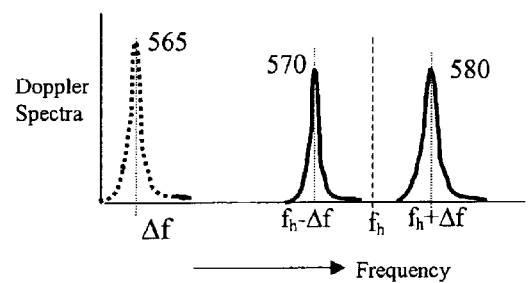
FIG. 5B shows the resulting spectra from the signal processing circuitry of FIG. 5A.
Figure 5A:
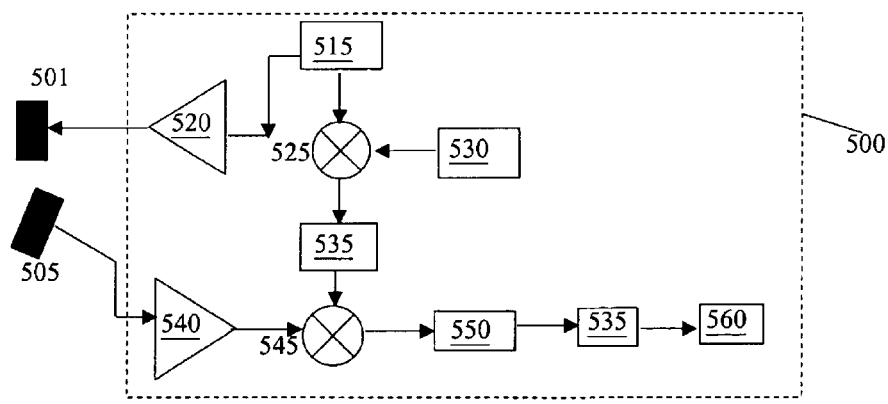
FIG. 5A shows a preferred embodiment of processing circuitry.

FIG. 5A shows a block diagram of possible signal processing circuitry used in determining flow velocity and direction, which may be used with any transmit/receive sensor arrangement. Transmitter 501 is driven by a reference oscillator 515 via a pre-amplifier 520. The oscillator 515 operates in either continuous or pulsed mode with a frequency of $f_0$, and is multiplied in a mixer 525 with frequency $f_h$, from a second oscillator 530. Oscillators 515 and 530 preferably are crystal referenced, high stability, low jitter oscillators like Pierce oscillators. The mixed product of $f_h$ and $f_0$ is then passes through a low pass filter 535 to produce a heterodyne reference frequency of $f_0$-$f_h$. The Doppler shifted signal returns through receiver 505 and is amplified by amplifier 540. The Doppler shifted signal frequency is $f_0$+$\Delta f$, where $\Delta f$ is the Doppler shift and can be either positive in the case of advancing flow in the annulus, or negative in the case of receding flow in the annulus. The Doppler shifted frequency and the heterodyne reference frequency are mixed using a mixer 545, then the mixed signal is passed through a low pass filter 550 to filter off the mixed portion of the signal above $2f_0$. The resulting signal is $f_h$+$\Delta f$. This result is passed through a notch filter 555 that is centered about the heterodyne frequency $f_h$ and has a passband of at least $2\Delta f$. This aids in suppressing large signal components at frequency $f_h$ and noise before the signal is processed using a Fast Fourier Transform 560 to determine spectral content. Resulting spectra from the Fast Fourier Transform 560 are depicted in FIG. 5B including the Doppler shift receding signal 570 or the advancing signal 580 centered about the heterodyne frequency. As a comparison, conventional coherent processing results in Doppler shift signal 565 and cannot reveal the directional information. Thus, with the use of heterodyne processing, both the velocity and the direction of flow may determined from the sign and magnitude of the spectral content information.

The Doppler frequency shift relative to the heterodyne frequency $f_h$ gives the direction of the flow. For example, if the resulting shifted heterodyne signal $f_h$+$\Delta f$ is less than the heterodyne frequency $f_h$, then the Doppler shift $\Delta f$ is negative, and the mud flow in the annulus is receding. Conversely, if the resulting shifted heterodyne signal $f_h$+$\Delta f$ is greater than the heterodyne frequency $f_h$, then the Doppler shift $\Delta f$ is positive, and the mud flow in the annulus is advancing. Further, the magnitude of the Doppler shift $\Delta f$ may be used to calculate the velocity of mud flow according to Equation 1.

$$V = c\left[\frac{(\Delta f)}{(\cos\theta_T + \cos\theta_R)f_0}\right] \quad (1)$$

Referring to Equation 1, c is the velocity of sound for mud that comes from sensor 13b or its equivalent. $\theta_T$ and $\theta_R$ are the angles of the transmitter and receive relative to the flow direction. It can be seen that any error in calculating the baseline speed of velocity measurement can result in an error in calculating the velocity of mud flow, therefore great care should be exercised when orienting the sensors on the drillstring. The Doppler shift is $\Delta f$, which is positive for mud flow advancing in the annulus and negative for mud flow receding in the annulus. The heterodyne frequency is $f_h$, and is generally on the same order of magnitude as (but different from) the transmitting frequency $f_0$. Heterodyne demodulation is more advantageous because it determines the flow direction information whereas coherent demodulation techniques only result in the positive-band frequency components and thus destroy the directional information. Secondly, since the Doppler frequency shift is offset by a heterodyne frequency $f_h$, the detection sensitivity for low Doppler shifts is dramatically enhanced. This is especially useful in slow flow situations such as mud loss while the recirculation pump is off. In slow flow situations the velocity in any direction (axial, radial, or tangential) may be small and high detection capability may be desired.

Figure 6B:
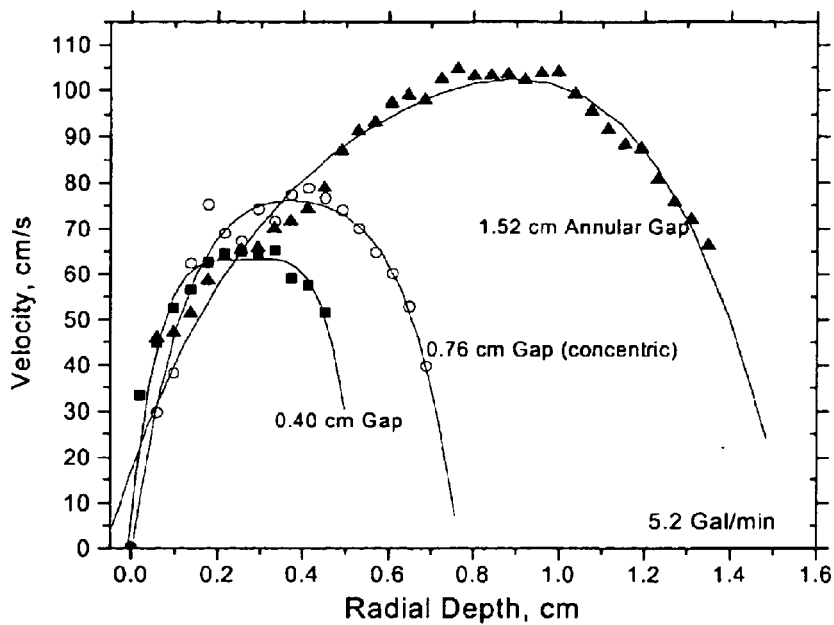
FIG. 6B shows experimental results for three annular gaps where the width of the gap between the outer pipe and inner pipe is 0.40, 0.76 (concentric), and 1.52 cm.
Figure 6A:
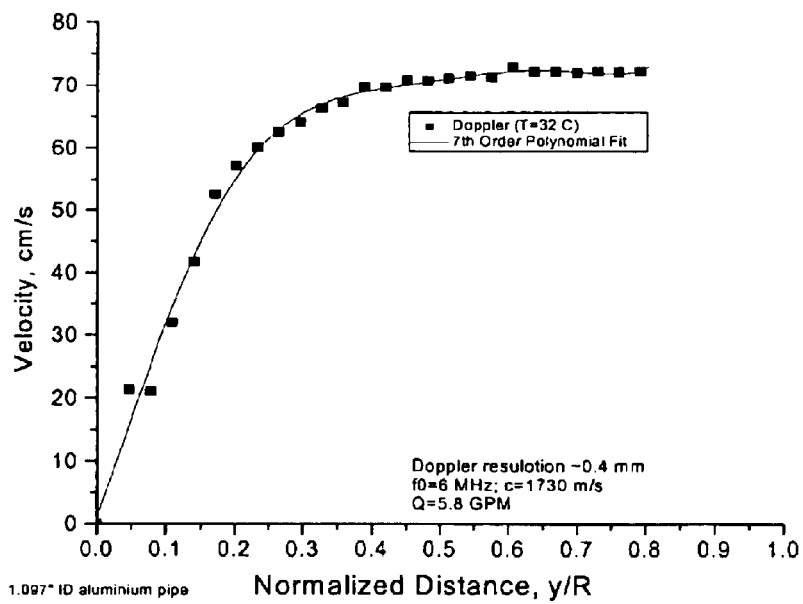
FIG. 6A shows experimental results for a 1 inch aluminum pipe.

FIG. 6A show velocity profiles of 8.6 lb./gal. water based mud in a 1 inch (inside diameter) circular pipe. FIG. 6B shows the velocity profiles for three annular gaps (0.40, 0.76, and 1.52 cm). The pulsed Doppler frequency is 6 MHz, the flow rate is 5.8 gpm (pipe flow) and 5.2 gpm (annular flow). The depth of investigation is up to about 0.6 inches.

The results in FIGS. 6a and 6b show that it is possible to measure flow velocity profile at different depths of investigation, and determine the yield stress of non-Newtonian fluids if a pressure drop measurement is available.

Many advantages and features arise from in situ downhole flow measurements. Currently downhole flow profile models are theoretical, but models based on actual downhole flow profiles may be constructed using the above disclosed system. This will help to understand actual downhole rheological downhole conditions (e.g., yield stress) and generate better hole cleaning practices.

Fractures in the formation may also be detected using the disclosed systems. For example, if mud is flowing out the annulus into the formation at a fracture point, and the radial flow out of the wellbore is measured, fracture orientation (including the three dimensional stress state of the reservoir) may be obtained. This technique may be further improved by integrating the sensors into repeaters in the drillstring such that multiple sensor measurements may be made at various points along the borehole.

In another embodiment, the in situ downhole flow parameters may be used in a feedback arrangement. For example, if the downhole sensors indicate that a well kick is occurring the mud flow rates may be adjusted to control pressure automatically using surface processing equipment. This technique would also prove useful in the event of a loss of circulation, where the mud flow may be stopped completely to prevent costly mud loss to the formation.

In another embodiment, the baseline speed of sound may be used to detect an influx of different fluids or gases. For example, if the speed of sound is measured in both the incoming mud flow and the outgoing mud flow in the annulus, and a gas reservoir is encountered while drilling such that gas is injected into the annulus, the difference between the incoming and out going speeds of sound will change indicating a possible reservoir was encountered. This is advantageous over conventional surface mud monitoring techniques in that the time required for the mud containing formation gas or fluid to reach the surface can be quite long, and is even more pronounced with deeper wells. Thus, by detecting mud composition changes real-time, drilling time can be saved, which translates into cost savings.

It is noted that the sensors disclosed herein have been described in terms of a two-transducer, transmitter-receiver system, i.e. with one transducer always acting as a transmitter and the other acting as a receiver. It is expected that these sensors may also be implemented as a single transducer that first transmits a sound pulse and then begins receiving. Further, this transmit/receive mode (sometimes called an XR mode) can also be applied in a two-transducer system, allowing the transducers to exchange roles as transmitter and receiver.

Numerous variations and modifications will become apparent to those skilled in the art once the above disclosure is fully appreciated. More specifically, although the term mud as used herein typically applies to over-balanced drilling operations, the embodiments disclosed herein equally apply to under-balanced drilling operations where other fluids may be used in lieu of mud.

In addition, other embodiments may combine the disclosed acoustic sensors with other circuitry in the drillstring, such as downhole repeaters. For example, the sensors may be combined with repeaters of the type discussed in "Telemetry Drill Pipe: Enabling Technology for the Downhole Internet", by Michael J Jellison et al., Society of Petroleum Engineers issue number 79885, which is incorporated herein by reference. Based on the telemetry type (e.g. acoustic, electromagnetic or telemetry with pre-wired drill pipe), the repeater type and the spacing between sensor/repeater combinations may be anywhere from several hundred feet to several thousand feet. With a plurality of such sensors distributed along the drillstring, it is possible to infer the profile of flow along the drillstring, thus helping to identify lost circulation zones or zones in which formation fluids are invading the borehole. It is intended that the following claims be interpreted to embrace all such variations and modifications.

What is claimed is:

1. A method of determining downhole fluid composition in an annulus, comprising:

measuring the in situ speed of sound of fluid inside a drillstring;

measuring the in situ speed of sound of fluid in the annulus;

comparing the speed of sound measurements; and determining fluid composition based on the comparison.

2. The method of claim 1, wherein the measurements are made with fluid circulation stopped.

3. The method of claim 1, wherein the measurements are made while drilling a formation.

4. The method of claim 1, further comprising detecting an influx of fluid or gases into the annulus based on fluid composition.

* * * * *